United States Patent [19]

Cantarore et al.

[11] Patent Number: 5,039,799
[45] Date of Patent: Aug. 13, 1991

[54] PIPERIDINE-TRIAZINE COMPOUNDS

[75] Inventors: Guiseppe Cantarore, Bitonto; Valerio Borzatta, Bologna; Franca Masina, Anzola Emilia, all of Italy

[73] Assignee: Ciba-Geigy Corporation, Ardsley, N.Y.

[21] Appl. No.: 410,192

[22] Filed: Sep. 20, 1989

[30] Foreign Application Priority Data

Sep. 23, 1988 [IT] Italy .................. 22052 A/88

[51] Int. Cl.$^5$ .......................................... C07D 401/14
[52] U.S. Cl. .................................. 544/113; 540/575; 540/598; 544/198; 544/207; 544/209; 544/212
[58] Field of Search ................. 540/598, 575; 544/113, 544/198, 207, 209, 212

[56] References Cited

U.S. PATENT DOCUMENTS

| 3,925,376 | 12/1975 | Chalmers et al. | 260/248 |
| 4,108,829 | 8/1978 | Cassandrini et al. | 260/45.8 NT |
| 4,288,593 | 9/1981 | Rody | 544/198 |
| 4,376,836 | 3/1983 | Wiezer et al. | 524/100 |
| 4,433,145 | 2/1984 | Wiezer et al. | 544/198 |
| 4,533,688 | 8/1985 | Toda et al. | 524/100 |
| 4,603,205 | 7/1986 | Neumann et al. | 546/16 |
| 4,703,072 | 10/1987 | Helwig et al. | 524/99 |

FOREIGN PATENT DOCUMENTS 0176106 4/1986 European Pat. Off. .
0209127 1/1987 European Pat. Off. .
0227640 7/1987 European Pat. Off. .

OTHER PUBLICATIONS

Chem. Abst. 105, 209942q Derwent No. 86-1899/62/30 (1986).

Primary Examiner—John M. Ford
Attorney, Agent, or Firm—Luther A. R. Hall

[57] ABSTRACT

The present invention relates to novel piperidine-triazine compounds of the general formula (I)

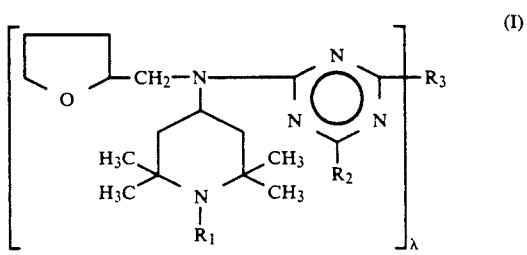

in which $R_1$ e.g. hydrogen or methyl, $\lambda$ is e.g. 1 and $R_2$ and $R_3$ are e.g. N-(2,2,6,6-tetramethyl-4-piperidyl)-tetrahydrofurfurylamino or 1,2,2,6,6-pentamethyl-4-piperidyloxy.

These compounds are effective as light stabilizers, heat stabilizers and oxidation stabilizers for organic materials.

7 Claims, No Drawings

PIPERIDINE-TRIAZINE COMPOUNDS

The present invention relates to novel piperidine-triazine compounds, to their use as light stabilizers, heat stabilizers and oxidation stabilizers for organic materials, in particular synthetic polymers, and to organic materials thus stabilized.

It is known that synthetic polymers are subject to photooxidative degradation when they are exposed to sunlight or other sources of ultraviolet light in the presence of oxygen. For their use in practice, it is therefore necessary to add to them suitable light stabilizers, such as certain benzophenone or benzotriazole derivatives, nickel complexes, substituted benzoic acid esters, alkylidenemalonates, cyanoacrylates, aromatic oxamides or sterically hindered amines.

Some triazine derivatives of 2,2,6,6-tetramethyl-4-piperidylamine and their use as stabilizers for synthetic polymers have been reported in U.S. Pat. Nos. 3,925,376, 4,108,829, 4,288,593, 4,376,836, 4,433,145 and 4,533,688, in European Patents 176,106, 209,127 and 227,640 and in Belgian Patent 904,401.

The present invention relates to triazine derivatives of N-(2,2,6,6-tetramethyl-4-piperidyl)-tetrahydrofurfurylamine, which, apart from being effective as light stabilizers for synthetic polymers, also show, surprisingly, an enhanced antioxidant action, especially in polyolefins.

In particular, the present invention relates to novel piperidine-triazine compounds of the general formula (I)

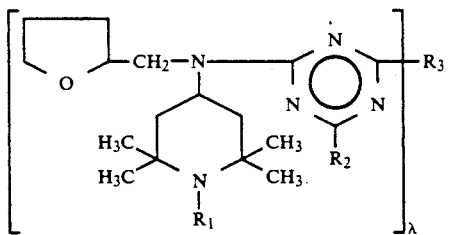

in which $R_1$ is hydrogen, $C_1$-$C_8$alkyl, $O^\cdot$, OH, NO, $CH_2CN$, $C_1$-$C_{18}$alkoxy, $C_5$-$C_{12}$cycloalkoxy, $C_3$-$C_6$alkenyl, $C_7$-$C_9$phenylalkyl which is unsubstituted or mono-, di- or tri-substituted on the phenyl by $C_1$-$C_4$alkyl, $C_1$-$C_8$-acyl or $C_2$-$C_4$alkyl substituted by OH in the 2-, 3- or 4-position, $R_2$ is a group —$OR_4$, —$SR_4$ or

in which $R_4$ is $C_1$-$C_{18}$alkyl, $C_5$-$C_{12}$cycloalkyl which is unsubstituted or mono-, di- or tri-substituted by $C_1$-$C_4$alkyl, $C_3$-$C_{18}$alkenyl, phenyl which is unsubstituted or mono-, di- or tri-substituted by $C_1$-$C_4$alkyl, $C_7$-$C_9$phenylalkyl which is unsubstituted or mono-, di-or tri-substituted on the phenyl by $C_1$-$C_4$alkyl, or a group of the formula (II)

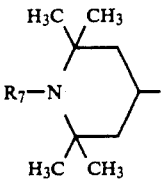

where $R_7$ has any of the definitions of $R_1$; $R_5$ and $R_6$ which can be identical or different are hydrogen, $C_1$-$C_{18}$alkyl, $C_5$-$C_{12}$cycloalkyl which is unsubstituted or mono-, di- or tri-substituted by $C_1$-$C_4$alkyl, $C_7$-$C_9$phenylalkyl which is unsubstituted or mono-, di- or tri-substituted on the phenyl by $C_1$-$C_4$alkyl, $C_2$-$C_4$alkyl which is substituted in the 2-, 3or 4-position by OH, by $C_1$-$C_8$alkoxy or by di-($C_1$-$C_4$alkyl)-amino, $C_3$-$C_{18}$alkenyl, tetrahydrofurfuryl or a group of the formula (II), or $R_5$ and $R_6$, together with the nitrogen atom to which they are linked, form part of a 5-membered to 7-membered heterocyclic ring, $\lambda$ is an integer from 1 to 6 and, if $\lambda$ is 1, $R_3$ has any of the definitions of $R_2$, with the proviso that $R_2$ and $R_3$ are different from

if both $R_5$ and $R_6$ are a group of the formula (II), and, if $\lambda$ is 2, $R_3$ is one of the groups of the formulae (IIIa)–(IIIc)

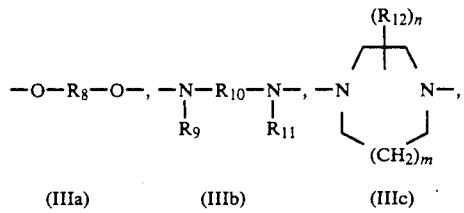

(IIIa)    (IIIb)    (IIIc)

in which $R_8$ is $C_2$-$C_{12}$alkylene, cyclohexylene, cyclohexylenedimethylene, methylenedicyclohexylene, ($C_2$-$C_6$alkylidene)-dicyclohexylene, phenylene, ($C_1$-$C_6$alkylidene)-diphenylene or xylylene, $R_9$ and $R_{11}$ which can be identical or different are hydrogen, $C_1$-$C_{18}$alkyl, $C_5$-$C_{12}$cycloalkyl which is unsubstituted or mono-, di- or tri-substituted by $C_1$-$C_4$alkyl, $C_7$-$C_9$phenylalkyl which is unsubstituted or mono-, di- or tri-substituted on the phenyl by $C_1$-$C_4$alkyl, or a group of the formula (II), $R_{10}$ is as defined above for $R_8$ or is $C_4$-$C_{12}$alkylene interrupted by 1, 2 or oxygen atoms or by 1 or 2 groups >N—$R_{13}$, where $R_{13}$ has any of the definitions of $R_9$ and $R_{11}$, or is one of the groups of the formulae (IVa)–(IVd)

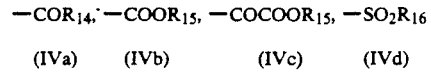

(IVa)    (IVb)    (IVc)    (IVd)

where $R_{14}$ is hydrogen, $C_1$-$C_{18}$alkyl, $C_5$-$C_{12}$cycloalkyl which is unsubstituted or mono-, di- or tri-substituted by $C_1$-$C_4$alkyl, $C_2$-$C_{18}$alkenyl, phenyl which is unsubstituted or mono-, di- or tri-substituted by $C_1$-$C_4$alkyl and/or an OH group, $C_7$-$C_9$phenylalkyl which is unsubstituted or mono-, di- or tri-substituted on the phenyl by $C_1$-$C_4$alkyl and/or an OH group, $R_{15}$ is $C_1$-$C_{18}$alkyl, $C_5$-$C_{12}$cycloalkyl which is unsubstituted or mono-, di-or tri-substituted by $C_1$-$C_4$alkyl, $C_3$-$C_{18}$alkenyl or a group of the formula (II) and $R_{16}$ is $C_1$-$C_{18}$alkyl or phenyl which is unsubstituted or mono-, di- or tri-substituted by $C_1$-$C_4$alkyl, m is zero or 1, $R_{12}$ is hydrogen or methyl and n is zero, 1, 2, 3 or 4, and, if $\lambda$ is 3, $R_3$ is one of the groups of the formulae (Va)-(Vc)

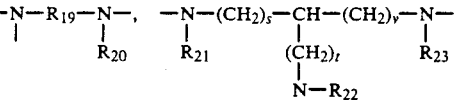

(Va)　　　　　　　(Vb)

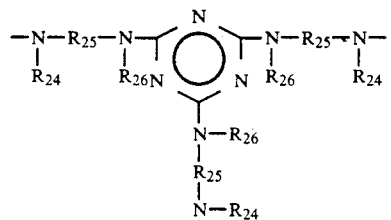

(Vc)

in which $R_{17}$, $R_{20}$, $R_{21}$, $R_{22}$, $R_{23}$, $R_{24}$ and $R_{26}$ which can be identical or different are as defined above for $R_9$ and $R_{11}$; $R_{18}$ and $R_{19}$ which can be identical or different are $C_2$-$C_{12}$alkylene or $C_4$-$C_{12}$alkylene interrupted by a group $>$N—$R_{27}$ with $R_{27}$ being as defined above for $R_{13}$, s and v which can be identical or different are integers from 2 to 6, t is zero or 1 and $R_{25}$ is $C_2$-$C_{12}$alkylene, and, if $\lambda$ is 4, 5 or 6, $R_3$ is a group of the formula

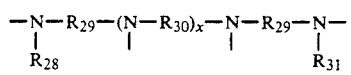

(VI)

in which $R_{28}$ and $R_{31}$ which can be identical or different are as defined above for $R_9$ and $R_{11}$; $R_{29}$ and $R_{30}$ which can be identical or different are $C_2$-$C_{12}$alkylene and x is 1, 2 or 3, and, if $\lambda$ is 4, $R_3$ is also one of the groups of the formulae (VIIa)-(VIIc)

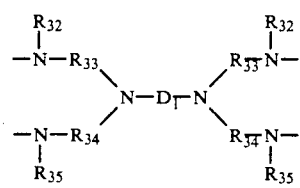

(VIIa)

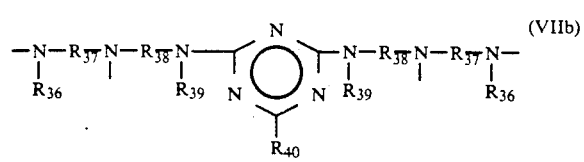

(VIIb)

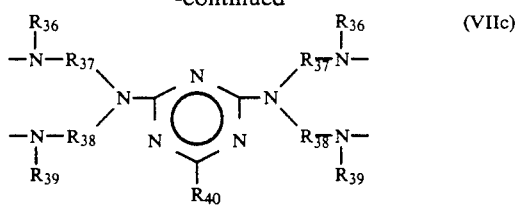

(VIIc)

in which $R_{32}$, $R_{35}$, $R_{36}$ and $R_{39}$ which can be identical or different are as defined above for $R_9$ and $R_{11}$; $R_{33}$, $R_{34}$, $R_{37}$ and $R_{38}$ which can be identical or different are $C_2$-$C_{12}$alkylene, $D_1$ is $C_2$-$C_{12}$alkylene, 2-hydroxytrimethylene, —CH$_2$CO—, xylylene or one of the groups of the formulae (VIIIa) and (VIIIb)

(VIIIa)　　　(VIIIb)

in which $R_{41}$ is a direct bond, $C_1$-$C_{12}$alkylene, cyclohexylene or phenylene and $R_{42}$ is as defined above for $R_8$, and $R_{40}$ is as defined above for $R_2$, and, if $\lambda$ is 6, $R_3$ is also one of the groups of the formulae (IXa)-(IXc)

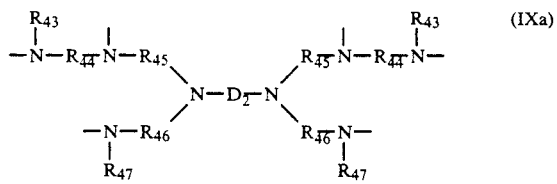

(IXa)

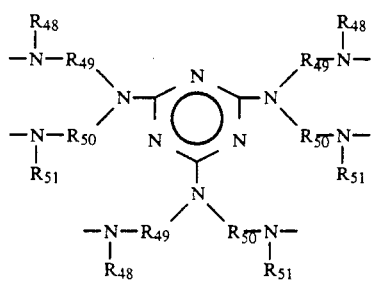

(IXb)

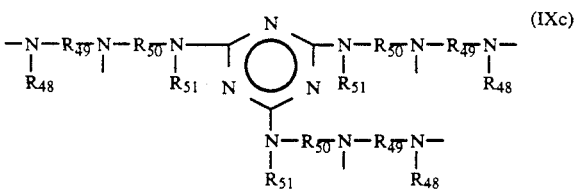

(IXc)

in which $R_{43}$, $R_{47}$, $R_{48}$ and $R_{51}$ which can be identical or different are as defined above for $R_9$ and $R_{11}$; $R_{44}$, $R_{45}$, $R_{46}$, $R_{49}$ and $R_{50}$ which can be identical or different are $C_2$-$C_{12}$alkylene and $D_2$ is as defined above for $D_1$.

Representative examples of $C_1$-$C_8$alkyl $R_1$ and $R_7$ are methyl, ethyl, propyl, butyl, isobutyl, pentyl, hexyl, heptyl and octyl. $C_1$-$C_4$alkyl, in particular methyl, is preferred.

Examples of $C_1$-$C_{18}$alkyl are methyl, ethyl, propyl, isopropyl, butyl, -butyl, isobutyl, t-butyl, pentyl, 2-pentyl, hexyl, heptyl, octyl, -ethylhexyl, t-octyl, nonyl, decyl, undecyl, dodecyl, tridecyl, tetradecyl, hexadecyl and octadecyl. $C_1$-$C_8$alkyl is preferred.

Examples of OH-substituted $C_2$-$C_4$alkyl are 2-hydroxyethyl, 2-hydroxypropyl, 3-hydroxypropyl, 2- hydroxybutyl and 4-hydroxybutyl. 2-Hydroxyethyl is preferred.

Examples of $C_2$-$C_4$alkyl substituted by $C_1$-$C_8$alkoxy, preferably $C_1$-$C_4$alkoxy, in particular methoxy or ethoxy, are 2-methoxyethyl, 2ethoxyethyl, 3-methoxypropyl, 3-ethoxypropyl, 3-butoxypropyl, 3-octoxypropyl and 4-methoxybutyl.

Examples of $C_2$-$C_4$alkyl substituted by di-($C_1$-$C_4$alkyl)-amino, preferably dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Representative examples of $C_1$-$C_{18}$alkoxy $R_1$ and $R_7$ are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$-$C_{12}$alkoxy, in particular heptoxy or octoxy, is preferred.

Examples of unsubstituted or substituted $C_5$-$C_{12}$cycloalkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Cyclohexyl which is unsubstituted or substituted by $C_1$-$C_4$alkyl is preferred.

Representative examples of $C_5$-$C_{12}$cycloalkoxy $R_1$ and $R_7$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having up to 18 carbon atoms are vinyl, allyl, 2-methylallyl, hexenyl, decenyl, undecenyl, heptadecenyl and oleyl. Allyl is one of the preferred definitions of $R_1$ and $R_7$. In alkenyl $R_1$, $R_4$, $R_5$, $R_6$, $R_7$ and $R_{15}$, the carbon atom in the 1-position is preferably a saturated carbon atom.

Examples of substituted phenyl are methylphenyl, dimethylphenyl, trimethylphenyl, t-butylphenyl, di-t-butylphenyl, hydroxyphenyl and 3,5-di-t-butyl-4-hydroxyphenyl.

Examples of phenylalkyl which is unsubstituted or substituted on the phenyl, are benzyl, methylbenzyl, dimethylbenzyl, t-butylbenzyl, 2-phenylethyl and 2-(3,5-di-t-butyl-4-hydroxyphenyl)-ethyl.

Acyl $R_1$ and $R_7$ having up to 8 carbon atoms can be aliphatic or aromatic.

Representative examples are formyl, acetyl, propionyl, butyryl, pentanoyl, hexanoyl, octanoyl, benzoyl, acryloyl and crotonyl. $C_1$-$C_8$Alkanoyl, $C_3$-$C_8$alkenoyl and benzoyl are preferred. Acetyl is particularly preferred.

If $R_5$ and $R_6$ which, together with the nitrogen atom to which they are linked, form part of a 5-membered to 7-membered heterocyclic ring, this heterocylic ring preferably contains a further hetero atom, for example nitrogen or oxygen. Representative examples are 1-pyrrolidyl, 1-piperidyl, 4-morpholinyl, 4-methyl-1-piperazinyl, 1-hexahydroazepinyl, 5,5,7-trimethyl-1-homopiperazinyl and 4,5,5,7-tetramethyl-1-homopiperazinyl. 4-Morpholinyl is preferred.

Examples of alkylene having up to 12 carbon atoms are methylene, ethylene, propylene, trimethylene, tetramethylene, pentamethylene, 2,2dimethyltrimethylene, hexamethylene, trimethylhexamethylene, decamethylene and dodecamethylene.

Examples of $C_4$-$C_{12}$alkylene interrupted by 1, 2 or 3 oxygen atoms are 3-oxapentane-1,5-diyl, 3,6-dioxaoctane-1,8-diyl and 3,6,9-trioxaundecane-1,11-diyl.

Representative examples of $C_4$-$C_{12}$alkylene $R_{10}$ interrupted by 1 or 2 groups $>$N—$R_{13}$ are the groups

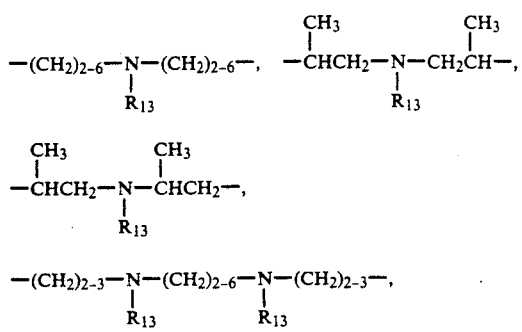

in which $R_{13}$ has any of the definitions given.

Representative examples of alkylene $R_{18}$ and $R_{19}$ interrupted by a group $>$N—$R_{27}$ are the groups

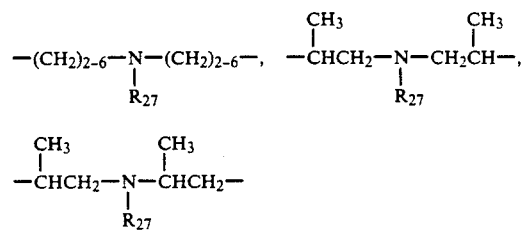

in which $R_{27}$ has any of the definitions given.

The preferred definitions of $R_1$ are hydrogen, $C_1$-$C_4$alkyl, OH, $C_6$-$C_{12}$alkoxy, $C_5$-$C_8$cycloalkoxy, allyl, benzyl, acetyl and 2-hydroxyethyl, in particular hydrogen and methyl.

Those compounds of the formula (I) are preferred in which $R_2$ is a group —$OR_4$, —$SR_4$ or

in which $R_4$ is $C_1$-$C_{18}$alkyl, $C_5$-$C_8$cycloalkyl which is unsubstituted or mono-, di- or tri-substituted by $C_1$-$C_4$alkyl, $C_3$-$C_{12}$alkenyl, phenyl, benzyl or a group of the formula (II), and $R_5$ and $R_6$ which can be identical or different are hydrogen, $C_1$-$C_{18}$alkyl, $C_5$-$C_8$cycloalkyl which is unsubstituted or mono-,di- or tri-substituted by $C_1$-$C_4$alkyl, benzyl, $C_2$-$C_3$alkyl substituted in the 2- or 3-position by OH, by $C_1$-$C_4$alkoxy or by di-($C_1$-$C_4$alkyl)-amino, allyl, oleyl, tetrahydrofurfuryl or a group of the formula (II), or the group

is 1-pyrrolidyl, 1-piperidyl, 4-morpholinyl or 1-hexahydroazepinyl, and $\lambda$ is an integer from 1 to 6, and, if $\lambda$ is 1, $R_3$ has any of the definitions of $R_2$ with the proviso that $R_2$ and $R_3$ are different from

if both $R_5$ and $R_6$ are a group of the formula (II), and, if $\lambda$ is 2, $R_3$ is one of the groups of the formulae (IIIa)–(IIIc) in which $R_8$ is $C_2$–$C_{10}$alkylene, cyclohexylene, cyclohexylenedimethylene, methylenedicyclohexylene, isopropylidenedicyclohexylene, phenylene or isopropylidenediphenylene, $R_9$ and $R_{11}$ which can be identical or different are hydrogen, $C_1$–$C_{12}$alkyl, $C_5$–$C_8$cycloalkyl which is - unsubstituted or mono-, di- or tri-substituted by $C_1$–$C_4$alkyl, benzyl or a group of the formula (II), $R_{10}$ is as defined above for $R_8$ or is $C_4$–$C_{12}$alkylene interrupted by 1, 2 or 3 oxygen atoms or by 1 or 2 groups $>N-R_{13}$ where $R_{13}$ has any of the definitions given for $R_9$ and $R_{11}$, or is one of the groups of the formulae (IVa)–(IVd) in which $R_{14}$ is hydrogen, $C_1$–$C_{17}$alkyl, $C_5$–$C_8$cycloalkyl which is unsubstituted or mono-, di- or tri-substituted by $C_1$–$C_4$alkyl, $C_2$–$C_{17}$alkenyl, phenyl which is unsubstituted or mono-, di- or tri-substituted by $C_1$–$C_4$alkyl and/or an OH group, $C_7$–$C_8$phenylalkyl which is unsubstituted or mono-, di- or tri-substituted on the phenyl by $C_1$–$C_4$alkyl and/or an OH group, $R_{15}$ is $C_1$–$C_{18}$alkyl, $C_5$–$C_8$cycloalkyl which is unsubstituted or mono-, di- or tri-substituted by $C_1$–$C_4$alkyl, $C_3$–$C_{18}$alkenyl or a group of the formula (II) and $R_{16}$ is $C_1$–$C_{12}$alkyl, phenyl or tolyl, m is zero or 1, $R_{12}$ is hydrogen or methyl and n is zero, 1, 2, 3 or 4, and, if $\lambda$ is 3, $R_3$ is one of the groups of the formulae (Va)–(Vc) in which $R_{17}$, $R_{20}$, $R_{21}$, $R_{22}$, $R_{23}$, $R_{24}$ and $R_{26}$ which can be identical or different are as defined above for $R_9$ and $R_{11}$; $R_{18}$ and $R_{19}$ which can be identical or different are $C_2$–$C_{10}$alkylene or $C_4$–$C_{12}$alkylene interrupted by a group $>N-R_{27}$ with $R_{27}$ being as defined above for $R_{13}$, s and v which can be identical or different are integers from 2 to 6, t is zero or 1 and $R_{25}$ is $C_2$–$C_{10}$alkylene, and, if $\lambda$ is 4, 5 or 6, $R_3$ is a group of the formula (VI) in which $R_{28}$ and $R_{31}$ which can be identical or different are as defined above for $R_9$ and $R_{11}$; $R_{29}$ and $R_{30}$ which can be identical or different are $C_2$–$C_{10}$alkylene and x is 1, 2 or 3, and, if $\lambda$ is 4, $R_3$ is also one of the groups of the formulae (VIIa)–(VIIc) in which $R_{32}$, $R_{35}$, $R_{36}$ and $R_{39}$ which can be identical or different are as defined above for $R_9$ and $R_{11}$; $R_{33}$, $R_{34}$, $R_{37}$ and $R_{38}$ which can be identical or different are $C_2$–$C_{10}$alkylene, $D_1$ is $C_2$–$C_{10}$alkylene, 2-hydroxytrimethylene, —CH$_2$CO—, xylylene or one of the groups of the formulae (VIIIa) or (VIIIb) in which $R_{41}$ is a direct bond or $C_1$–$C_{10}$alkylene, $R_{42}$ is as defined above for $R_8$, and $R_{40}$ is as defined above for $R_2$, and, if $\lambda$ is 6, $R_3$ is also one of the groups of the formulae (IXa)–(IXc) in which $R_{43}$, $R_{47}$, $R_{48}$ and $R_{51}$ which can be identical or different are as defined above for $R_9$ and $R_{11}$; $R_{44}$, $R_{45}$, $R_{46}$, $R_{49}$ and $R_{50}$ which can be identical or different are $C_2$–$C_{10}$alkylene and $D_2$ is as defined above for $D_1$.

Those compounds of the formula (I) are particularly preferred in which $R_2$ is a group —OR$_4$ or

in which $R_4$ is $C_1$–$C_{12}$alkyl, cyclohexyl which is unsubstituted or mono-, di- or tri-substituted by $C_1$–$C_4$alkyl, allyl, undecenyl, phenyl, benzyl or a group of the formula (II), $R_5$ and $R_6$ which can be identical or different are hydrogen, $C_1$–$C_{12}$alkyl, cyclohexyl which is unsubstituted or mono-, di- or tri-substituted by $C_1$–$C_4$alkyl, benzyl, $C_2$–$C_3$alkyl which is substituted in the 2- or 3-position by OH, by methoxy, by ethoxy, by dimethylamino or by diethylamino, allyl, tetrahydrofurfuryl or a group of the formula (II), or the group

is 4-morpholinyl, and l is an integer from 1 to 6, and, if $\lambda$ is 1, $R_3$ has any of the definitions given for $R_2$, with the proviso that $R_2$ and $R_3$ are different from

if both $R_5$ and $R_6$ are a group of the formula (II), and if $\lambda$ 2, $R_3$ is one of the groups of the formulae (IIIb)–(IIIc) in which $R_9$ and $R_{11}$ which can be identical or different are hydrogen, $C_1$–$C_8$alkyl, cyclohexyl which is unsubstituted or mono-, di- or tri-substituted by $C_1$–$C_4$alkyl, benzyl or a group of the formula (II), $R_{10}$ is $C_2$–$C_8$alkylene, cyclohexylenedimethylene, methylenedicyclohexylene, $C_4$–$C_{10}$alkylene interrupted by 1 or 2 oxygen atoms or $C_4$–$C_{12}$alkylene interrupted by 1 or 2 groups $>N-R_{13}$ where $R_{13}$ has any of the definitions given for $R_9$ and $R_{11}$, or is one of the groups of the formulae (IVa)–(IVc) in which $R_{14}$ is $C_1$–$C_{12}$alkyl, cyclohexyl which is unsubstituted or mono-, di- or tri-substituted by $C_1$–$C_4$alkyl, $C_2$–$C_{10}$alkenyl, phenyl, 3,5-di-t-butyl-4-hydroxyphenyl, benzyl or 2-(3,5-di-t-butyl-4-hydroxyphenyl)-ethyl, $R_{15}$ is $C_1$–$C_{12}$alkyl, cyclohexyl which is unsubstituted or mono-, di- or tri-substituted by $C_1$–$C_4$alkyl, allyl, undecenyl, oleyl or a group of the formula (II), m is zero or 1, $R_{12}$ is hydrogen or methyl and n is zero, 1, 2 or 3, and, if $\lambda$ is 3, $R_3$ is a group of the formula (Va) in which $R_{17}$ and $R_{20}$ which can be identical or different are as defined above for $R_9$ and $R_{11}$; $R_{18}$ and $R_{19}$ which can be identical or different are $C_2$–$C_8$alkylene and $R_{18}$ is also $C_4$–$C_{12}$alkylene interrupted by a group $>N-R_{27}$ with $R_{27}$ being as defined above for $R_{13}$, and, if $\lambda$ is 4, 5 or 6, $R_3$ is a group of the formula (VI) in which $R_{28}$ and $R_{31}$ which can be identical or different are as defined above for $R_9$ and $R_{11}$; $R_{29}$ and $R_{30}$ which can be identical or different are $C_2$–$C_8$alkylene and x is 1, 2 or 3, and, if $\lambda$ is 4, $R_3$ is also a group of the formula (VIIa) in which $R_{32}$ and $R_{35}$ which can be identical or different are as defined above for $R_9$ and $R_{11}$; $R_{33}$ and $R_{34}$ which can be identical or different are $C_2$–$C_8$alkylene and $D_1$ is $C_2$–$C_8$alkylene, 2-hydroxytrimethylene, xylylene or a group of the formula (VIIIa) or (VIIIb) in which $R_{41}$ is a direct bond or $C_1$–$C_8$alkylene and $R_{42}$ is $C_4$–$C_8$alkylene, 3-oxapentane-1,5-diyl, cyclohexylenedimethylene or isopropylidenedicyclohexylene, and, if $\lambda$ is 6, $R_3$ is also a group of the formula (IXa) in which $R_{43}$ and $R_{47}$ which can be identical or different are as defined above for $R_9$ and $R_{11}$; $R_{44}$, $R_{45}$ and $R_{46}$ which can be identical or different are $C_2$–$C_8$alkylene and $D_2$ is as defined above for $D_1$.

Those compounds of the formula (I) are of special interest in which $R_2$ is a group —OR$_4$ or

in which $R_4$ is $C_1$–$C_8$alkyl, cyclohexyl, allyl, phenyl, benzyl, 2,2,6,6-tetramethyl-4-piperidyl or 1,2,2,6,6-pentamethyl4-piperidyl, $R_5$ and $R_6$ which can be identical or different are $C_1$–$C_8$alkyl, cyclohexyl, benzyl, $C_2$–C-

$_3$alkyl substituted in the 2- or 3-position by methoxy, by ethoxy, by dimethylamino or by diethylamino, allyl, tetrahydrofurfuryl, 2,2,6,6-tetramethyl-4-piperidyl or 1,2,2,6,6-pentamethyl-4-piperidyl, or $R_5$ is also hydrogen, or the group

is 4-morpholinyl, and $\lambda$ is 1, 2, 3 or 4, and, if $\lambda$ is 1, $R_3$ has any of the definitions given for $R_2$, with the proviso that $R_2$ and $R_3$ are different from

if both $R_5$ and $R_6$ are a group of the formula (II), and, if $\lambda$ is 2, $R_3$ is one of the groups of the formulae (IIIb)—(IIIc) in which $R_9$ and $R_{11}$ which can be identical or different are hydrogen, $C_1$–$C_4$alkyl, cyclohexyl, 2,2,6,6-tetramethyl-4-piperidyl or 1,2,2,6,6-pentamethyl-4-piperidyl, $R_{10}$ is $C_2$–$C_6$alkylene, cyclohexylenedimethylene, methylenedicyclohexylene, $C_4$–$C_{10}$alkylene interrupted by 1 or 2 oxygen atoms or $C_4$–$C_{12}$alkylene interrupted by 1 or 2 groups >N—$R_{13}$ in which $R_{13}$ is hydrogen, methyl or a group of the formula (IVa) or (IVb) in which $R_{14}$ is $C_1$–$C_8$alkyl, cyclohexyl, phenyl or 2-(3,5-di-t-butyl-4-hydroxyphenyl)-ethyl and $R_{15}$ is $C_1$–$C_8$alkyl, cyclohexyl, t-butylcyclohexyl or 1,2,2,6,6-pentamethyl-4-piperidyl, and m and n are zero, and, if $\lambda$ is 3, $R_3$ is a group of the formula (Va) in which $R_{17}$ and $R_{20}$ which can be identical or different are as defined above for $R_9$ and $R_{11}$; $R_{18}$ and $R_{19}$ which can be identical or different are $C_2$–$C_6$alkylene and $R_{18}$ is also $C_4$–$C_6$alkylene interrupted by a group >N—$R_{27}$ with $R_{27}$ being as defined above for $R_{13}$, and, if $\lambda$ is 4, $R_3$ is a group of the formula (VI) in which $R_{28}$ and $R_{31}$ which can be identical or different are as defined above for $R_9$ and $R_{11}$; $R_{29}$ and $R_{30}$ which can be identical or different are $C_2$–$C_6$alkylene and x is 1, or $R_3$ is a group of the formula (VIIa) in which $R_{32}$ and $R_{35}$ which can be identical or different are as defined above for $R_9$ and $R_{11}$; $R_{33}$ and $R_{34}$ which can be identical or different are $C_2$–$C_6$alkylene and $D_1$ is a group of the formula (VIIIa) or (VIIIb) in which $R_{41}$ is a direct bond or $C_1$–$C_4$alkylene and $R_{42}$ is $C_4$–$C_6$alkylene.

Those compounds of the formula (I) are of particular interest in which $R_1$ is hydrogen or methyl, $R_2$ is a group —$OR_4$ or

in which $R_4$ is $C_1$–$C_4$alkyl, 2,2,6,6-tetramethyl-4-piperidyl or 1,2,2,6,6-pentamethyl4-piperidyl, $R_5$ and $R_6$ which can be identical or different are $C_1$–$C_8$alkyl, allyl, tetrahydrofurfuryl, 2,2,6,6-tetramethyl-4-piperidyl or 1,2,2,6,6-pentamethyl-4-piperidyl, or $R_5$ is also hydrogen, or the group

is 4-morpholinyl, and $\lambda$ is 1, 2, 3 or 4, and, if $\lambda$ is 1, $R_3$ has any of the definitions given for $R_2$, with the proviso that $R_2$ and $R_3$ are different from bis-(2,2,6,6-tetramethyl-4-piperidyl)-amino and bis-(1,2,2,6,6-pentamethyl-4-piperidyl)-amino, and, if $\lambda$ is 2, $R_3$ is one of the groups of the formulae (IIIb)—(IIIc) in which $R_9$ and $R_{11}$ which can be identical or different are hydrogen, methyl, 2,2,6,6-tetramethyl-4-piperidyl or 1,2,2,6,6-pentamethyl-4-piperidyl, $R_{10}$ is $C_2$–$C_6$alkylene or $C_4$–$C_6$alkylene interrupted by a group >N—$R_{13}$ where $R_{13}$ is hydrogen, methyl or a group of the formula (IVa) or (IVb) in which $R_{14}$ and $R_{15}$ are $C_1$–$C_4$alkyl, and m and n are zero, and, if $\lambda$ is 3, $R_3$ is a group of the formula (Va) in which $R_{17}$ and $R_{20}$ which can be identical or different are as defined above for $R_9$ and $R_{11}$; $R_{18}$ and $R_{19}$ which can be identical or different are $C_2$–$C_6$alkylene, and $R_{18}$ is also $C_4$–$C_6$alkylene interrupted by a group >N—$R_{27}$ with $R_{27}$ being as defined above for $R_{13}$, and if $\lambda$ is 4, $R_3$ is a group of the formula (VI) in which $R_{28}$ and $R_{31}$ which can be identical or different are hydrogen or methyl, $R_{29}$ and $R_{30}$ which can be identical or different are $C_2$–$C_3$alkylene and x is 1, or $R_3$ is a group of the formula (VIIa) in which $R_{32}$ and $R_{35}$ which can be identical or different are hydrogen, methyl, 2,2,6,6-tetramethyl-4-piperidyl or 1,2,2,6,6-pentamethyl-4-piperidyl, $R_{33}$ and $R_{34}$ which can be identical or different are $C_2$–$C_6$alkylene and $D_1$ is a group of the formula (VIIIa) or (VIIIb) in which $R_{41}$ is a direct bond or $C_1$–$C_4$alkylene and $R_{42}$ is tetramethylene or hexamethylene.

The compounds of the formula (I) can be prepared according to processes known per se, for example as described in U.S. Pat. Nos. 3,925,376 and 4,108,829, by reacting, in any order, cyanuric chloride with compounds of the formulae (Xa)–(Xc)

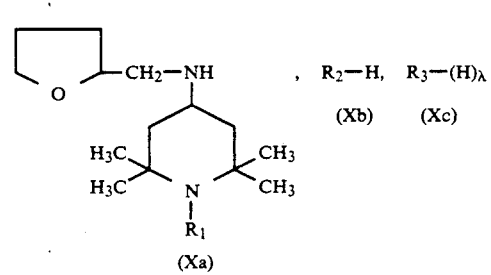

in the appropriate molar ratios.

If $R_{10}$, $R_{18}$ and $R_{19}$ are $C_4$–$C_{12}$alkylene interrupted by 1 or 2 groups >N—$R_{13}$ or by a group >N—$R_{27}$, the compounds of the formula (I) are preferably prepared by reacting the corresponding compounds with $R_{13}$ and $R_{27}$=H with suitable alkylating or acylating reagents.

If $R_3$ is a group of the formula (VIIa) or (IXa), the compounds of the formula (I) are preferably prepared by reacting a compound of the formula (XIa) or (XIb)

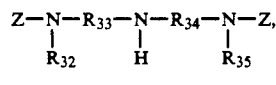

(XIa)

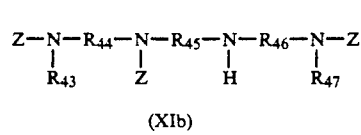

(XIb)

in which Z is a group of the formula (XII)

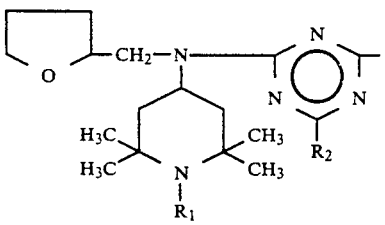

(XII)

with a compound of the formula (XIII)

W—D—W   (XIII)

in which W is preferably chlorine or bromine and D is as defined above for $D_1$ or $D_2$, or with epichlorohydric if $D_1$ and $D_2$ are 2-hydroxytrimethylene.

If $R_1$ is methyl, the compounds of the formula (I) are preferably prepared by reacting the corresponding compounds with $R_1=H$ with formaldehyde and formic acid or with formaldehyde and hydrogen in the presence of a hydrogenation catalyst, for example palladium or platinum. In these reactions, the amine non-piperidine >NH groups and, under certain conditions, also the melamine >NH groups which may be present can also be methylated.

The reactions of cyanuric chloride with the compounds of the formulae (Xa)–(Xc) are preferably carried out in an aromatic hydrocarbon solvent, for example toluene, xylene or trimethylbenzene, operating at temperatures from e.g. $-20°$ to $40°$ C., preferably from $-10°$ to $20°$ C., for the substitution of the first Cl, from e.g. $40°$ to $100°$ C., preferably from $50°$ to $90°$ C., for the substitution of the second Cl, and from e.g. $100°$ to $200°$ C., preferably from $120°$ to $180°$ C., for the substitution of the third Cl.

The hydrohalic acid released in the various reactions is neutralized preferably by an inorganic base, for example sodium or potassium hydroxide or carbonate in quantities at least equivalent to the acid released.

The compounds of the formula (Xa) can be prepared according to processes known for the reductive amination of a piperidone of the formula (XIV)

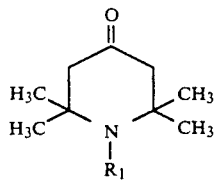

(XIV)

with tetrahydrofurfurylamine in the presence of a hydrogenation catalyst, such as e.g. platinum, palladium or nickel. The other intermediates used, of the formulae (Xb) and (Xc), are commercial products or products which can be prepared according to known processes.

As mentioned at the outset, the compounds of the formula (I) are highly effective in improving the light stability, heat stability and oxidation stability of organic materials, in particular synthetic polymers and copolymers.

Examples of such organic materials which can be stabilized are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/ butene-1, propylene/butadiene, isobutylene/isoprene, ethylene/alkyl acrylates, ethylene/alkyl methacrylates, ethylene/vinyl acetate or ethylene/ acrylic acid copolymers and their salts (ionomers) and terpolymers of ethylene with propylene and a diene, such as hexadiene, dicyclopentadiene or ethylidenenorbornene; as well as mixtures of such copolymers and their mixtures with polymers mentioned in 1) above, for example polypropylene/ethylene-propylene copolymers, LDPE/EVA, LDPE/EAA, LLDPE/EVA and LLDPE/EAA.

3a. Hydrocarbon resins (for example $C_5$–$C_9$) and hydrogenated modifications thereof (for example tackyfiers).

4. Polystyrene, poly-(p-methylstyrene), poly-($\alpha$-methylstyrene).

5. Copolymers of styrene or $\alpha$-methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/ styrene, styrene/isoprene/styrene, styrene/ethylene/-butylene/styrene or styrene/ethylene/propylene/styrene.

6. Graft copolymers of styrene or $\alpha$-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS, MBS, ASA or AES polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example polyvinyl chloride, polyvinylidene chloride, polyvinyl fluoride, polyvinylidene fluoride, as well as copolymers thereof, as for example vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/ butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one hand and on the other hand aliphatic or aromatic polyisocyanates, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylylenediamine and adipic acid; polyamides prepared from hexamethylenediamine and isophthalic or/and terephthalic acid and optionally an elastomer as modifier, for example poly-2,4,4-trimethylhexamethylene-terephthalamide or poly-m-phenylene-isophthalamide. Further, copolymers of the aforementioned polyamides with polyolefins, olefin copolymers, ionomers or chemically bonded or grafted elastomers; or with polyethers, such as for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2-(4-hydroxyphenyl)-propane]terephthalate and polyhydroxybenzoates as well as block copolyetheresters derived from polyethers having hydroxyl end groups.

18. Polycarbonates and polyester-carbonates.

19. Polysulfones, polyether-sulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyesteracrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer-homologous manner, such as cellulose acetates, cellulose propionates and cellulose butyrates, or cellulose ethers, such as methylcellulose; rosins and their derivatives.

27. Mixtures of polymers as mentioned above, for example PP/EPDM, polyamide 6/EPDM or ABS, PVC/EVA, PVC/ABS, PVC/MBS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubbers, for example natural latex or latexes of carboxylated styrene/butadiene copolymers.

The compounds of the formula (I) are particularly suitable for improving the light stability, heat stability and oxidation stability of polyolefins, especially polyethylene and polypropylene. The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably from 0.05 to 1%.

The compounds of the formula (I) can be incorporated in the polymeric materials by various processes, such as e.g. dry mixing in the form of powder, or wet mixing in the form of solutions or suspensions or also in the form of a masterbatch; in such operations, the polymer can be used in the form of powder, granules, solutions, suspensions or in the form of latices.

The materials stabilized with the products of the formula (I) can be used for the production of moldings, films, tapes, monofilaments, surface coatings and the like.

If desired, other conventional additives for synthetic polymers, such as e.g. antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the organic materials.

Particular examples of additives which can be used in a mixture with the compounds of the formula (I) are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tertbutylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-1,1.3 -tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3,-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, for example lauric acid 4-hydroxyanilide, stearic acid 4-hydroxyanilide, 2,4-bis(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

2. UV absorbers and light stabilizers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3', 5'-di-tert-butyl, 5-chloro-3'-tert-butyl-5'-methyl, 3'-sec-butyl-5'-tert-butyl, 4'-octoxy,3',5'-di-tert-amyl and 3',5'-bis(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β methyl-p-methoxycinnamate, butyl α-cyano-β-methyl-p-methoxycinnamate, methyl α-carbomethoxy-p-methoxycinnamate and N-(β-carbo-methoxy-β-cyanovinyl)-2-methylindoline.

2.5. Nickel compounds, for example nickel complexes of 2,2'-thiobis[4(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis-(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'- bis(2,2,6,6-tetramethyl-4-piperidyl)hexamethylenediamine and 4-tert-octylamino-2,6-dichloro-1,3,5-triazine, tris(2,2,6,6-tetra-methyl-4-piperidyl) nitrilotriacetate, tetrakis(2,2,6,6-tetramethyl-4piperidyl) 1,2,3,4-butanetetracarboxylate, 1,1'-(1,2-ethanediyl)bis(3,3,5,5-tetramethylpiperazinone).

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tertbutyloxanilide, 2-ethoxy-2'-ethyloxanilide, N,N'-bis(3-dimethylaminopropyl)oxalamide, 2-ethoxy-5-tert-butyl-2'-ethyloxanilide and its mixtures with 2-ethoxy-2'-ethyl-5,4'-di-tert-butyloxanilide and mixtures of ortho- and paramethoxy-disubstituted oxanilides and mixtures of o- and p-ethoxy-disubstituted oxanilides.

2.8. 2-(2-Hydroxyphenyl)-1,3.5-triazines, for example 2,4,6-tris(2-hydroxy-4-octyloxyphenyl)-1,3,5-triazine, 2-(2-hydroxy-4-octyloxy-phenyl)-4,6-bis(2,4-dimethylphenyl)-1,3,5-triazine, 2-(2,4-dihydroxy-phenyl)-4,6-bis(2,4-dimethylphenyl)-1,3,5-triazine, 2,4-bis(2-hydroxy4-propyloxyphenyl)-6-(2,4-dimethylphenyl)-1,3,5-triazine, 2-(2-hydroxy4-octyloxyphenyl)-4,6-bis(4-methylphenyl)-1,3,5-triazine, 2-(2-hydroxy4-dodecyloxyphenyl)-4,6-bis(2,4-dimethylphenyl)-1,3,5-triazine.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl)4,4'-biphenylenediphosphonite, 3,9-bis(2,4-di-tert-butylphenoxy)-2,4,8,10-tetraoxa-3,9-diphosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example Ca stearate, Zn stearate, Mg stearate, Na ricinoleate and K palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibers, asbestos, talc, kaolin, mica, barium sulfate, metal oxides and hydroxides, carbon black, graphite.

10. Other additives, for example plasticizers, lubricants, emulsifiers, pigments, optical brighteners, flameproofing agents, antistatic agents and blowing agents.

In order to illustrate the present invention more clearly, several examples of the preparation of compounds of the formula (I) are described below; these examples are given by way of illustration only and do not imply any restriction.

Particularly preferred compounds of formula (I) are those of Examples 2, 5, 7, 13 and 22.

EXAMPLE 1

Preparation of the compound

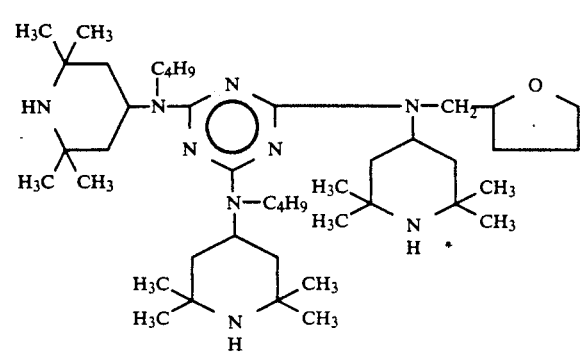

80.43 g (0.15 mol) of 2-chloro-4,6-bis-[N-(2,2,6,6-tetramethyl-4-piperidyl)-butylamino]-1,3,5-triazine, 36.06 g (0.15 mol) of N-(2,2,6,6-tetramethyl-4-piperidyl)-tetrahydrofurfurylamine and 12 g (0.3 mol) of sodium hydroxide in 250 ml of mesitylene are heated under reflux for 20 hours, with azeotropic removal of the water of reaction.

The mixture is cooled to about 50° C. and filtered, and the filtrate is washed with water. The solution is then dried over sodium sulfate and evaporated in vacuo (2 mbar).

The residue is taken up in n-hexane, from which the product of melting point 118°–120° C. crystallizes.

Analysis for $C_{43}H_{81}N_9O$. Calculated: C=69.68%; H=11.15%; N=17.01%. Found: C=68.75%; H=10.95%; N=17.02%.

EXAMPLE 2

Preparation of the compound

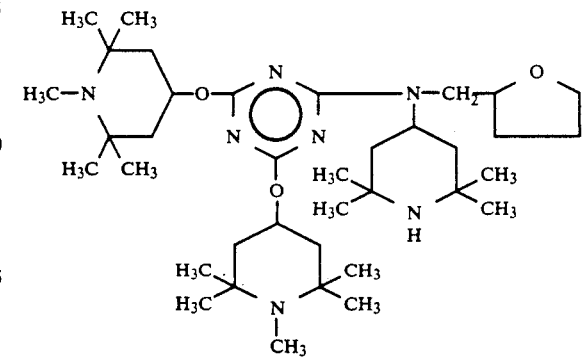

36.0 g (0.15 mol) of N-(2,2,6,6-tetramethyl-4-piperidyl)tetrahydrofurfurylamine are added slowly to a solution of 27.67 g (0.15 mol) of cyanuric chloride in 150 ml of xylene, the temperature being maintained at 10° C.

After stirring for one hour at ambient temperature, the mixture is cooled to 10° C., and a solution of 6.00 g (0.15 mol) of sodium hydroxide in 50 ml of water is added.

The mixture is stirred for 2 hours at ambient temperature, the aqueous phase is separated off, and 53.10 g (0.31 mol) of 1,2,2,6,6-pentamethyl4-piperidinol dissolved in 100 ml of xylene are added to the organic solution.

The mixture is heated for 4 hours under reflux, 12.60 g (0.31 mol) of sodium hydroxide are added, and the mixture is then heated under reflux for 18 hours with azeotropic removal of the water of reaction.

The mixture is then cooled to about 50° C., filtered, washed twice with 100 ml of water at 60° C. and, after drying with sodium sulfate, evaporated in vacuo (2 mbar).

The residue is treated with n-hexane, from which the product of melting point 87°–90° C. crystallizes.

Analysis for $C_{37}H_{67}N_7O_3$. Calculated: C=67.54%; H=10.26%; N=14.90%. Found: C=66.99%; H=10.21%; N=14.79%.

EXAMPLE 3

Preparation of the compound

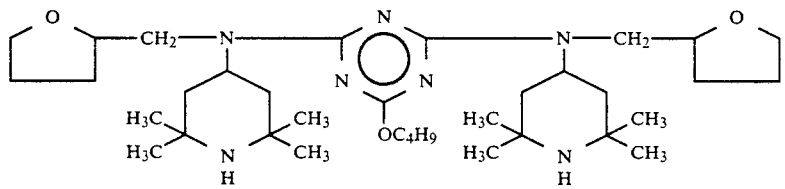

22.20 g (0.1 mol) of 2-butoxy-4,6-dichloro-1,3,5-triazine, 48.08 g (0.2 mol) of N-(2,2,6,6-tetramethyl-.-4piperidyl)-tetrahydrofurfurylamine and 500 ml of xylene are heated for 2 hours at 90° C.

12.00 g (0.3 mol) of sodium hydroxide are added, and the mixture is heated under reflux for 18 hours, with azeotropic removal of the water of reaction.

The mixture is cooled to about 50° C., filtered and evaporated in vacuo (2 mbar).

The product has a melting point of 130°–131° C.

Analysis for $C_{35}H_{63}N_7O_3$. Calculated: C=66.75%; H=10.07%; N=15.56%. Found: C=66.55%; H=10.09%; N=15.62%.

EXAMPLES 4–6: Following the procedure described in Example 3 and using the appropriate reagents, the following compounds of the formula

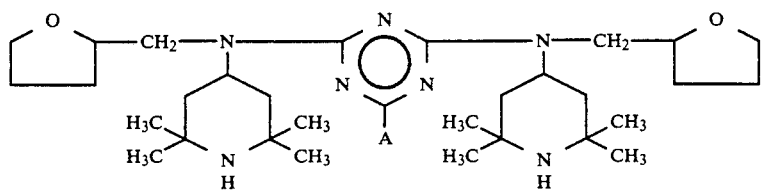

are prepared:

| Example | A | Melting point (°C.) |
|---|---|---|
| 4 | 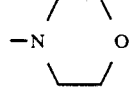 | 124–126 |
| 5 | 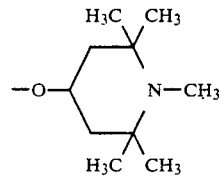 | 78–80 |
| 6 | 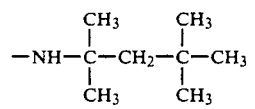 | 77–79 |

EXAMPLE 7

Preparation of the compound

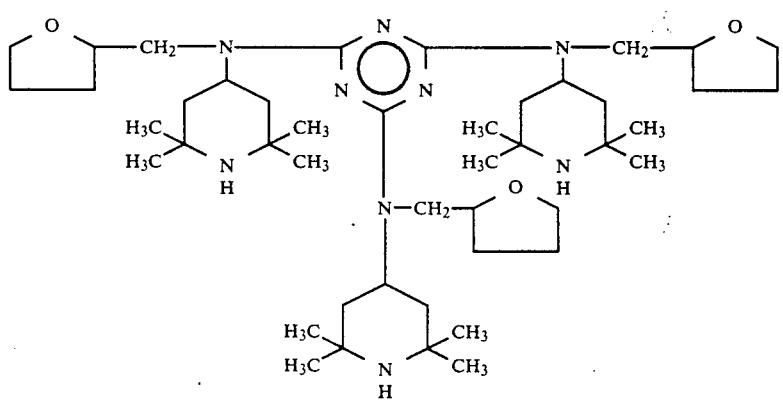

108.17 g (0.45 mol) of N-(2,2,6,6-tetramethyl-4-piperidyl)-tetrahydrofurfurylamine are slowly added to a solution of 27.67 g (0.15 mol) of cyanuric chloride in 30 ml of mesitylene, the temperature being maintained at 0° C.

The mixture is heated for 4 hours at 60° C., 25.20 g (0.63 mol) of sodium hydroxide are added, and the mixture is heated under reflux for 18 hours, with azeotropic removal of the water of reaction.

The mixture is then cooled to 60° C., filtered and evaporated in vacuo (2 mbar).

The residue is then treated with acetonitrile, and the product thus obtained has a melting point of 101°-103° C.

Analysis for $C_{45}H_{81}N_9O_3$. Calculated: C=67.88%; H=10.25%; N=15.83%. Found: C=66.48%; H=10.06%; N=15.60%.

EXAMPLE 8

Preparation of the compound

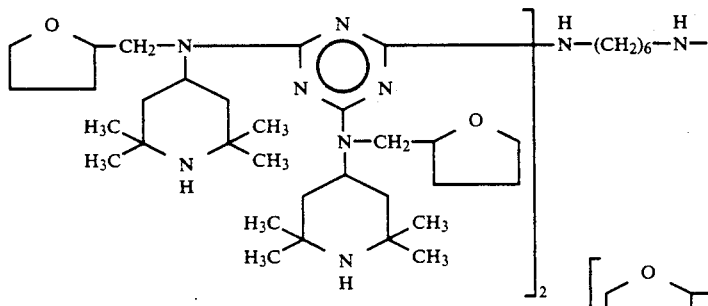

48.08 g (0.2 mol) of 2,2,6,6-tetramethyl-4-piperidyl)-tetrahydrofurfurylamine are added slowly to a solution of 18.44 g (0.1 mol) of cyanuric chloride in 200 ml of mesitylene, cooled to 10° C.

The mixture is then heated for 1 hour to 50° C.

After cooling to ambient temperature, a solution of 8.80 g (0.22 mol) of sodium hydroxide in 50 ml of water is added, and the mixture is heated for 3 hours at 80° C.

The aqueous phase is separated off, and 5.81 g (0.05 mol) of 1,6-hexanediamine are added.

The mixture is heated for 4 hours under reflux and cooled, 8.80 g (0.22 mol) of powdered sodium hydroxide are added and the mixture is heated under reflux for 14 hours, with azeotropic separation of the water of reaction.

After cooling to ambient temperature, the reaction mixture is filtered and evaporated in vacuo (2 mbar). The residue is taken up in octane in the presence of a small quantity of water, from which the product of melting point 114°-116° C. crystallizes.

Analysis for $C_{68}H_{122}N_{26}O_4$. Calculated: C=66.56%; H=10.01%; N=18.26%. Found: C=66.49%; H=9.9%; N=17.82%.

EXAMPLES 9

Following the procedure described in Example 8, but using the appropriate reagents, the following compounds of the formula

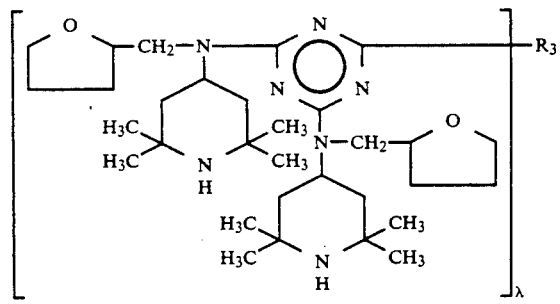

are prepared:

| Example | λ | R₃ | Melting point (°C.) |
|---|---|---|---|
| 9 | 2 | —N—(CH₂)₆—N— with 2,2,6,6-tetramethylpiperidyl groups on each N | 268–270 |
| 10 | 3 | —NH—(CH₂)₂—NH—(CH₂)₂—NH— | 121–123 |
| 11 | 4 | —NH—(CH₂)₃—NH—(CH₂)₂—NH—(CH₂)₃—NH— | 156–158 |

EXAMPLE 12

Preparation of the compound

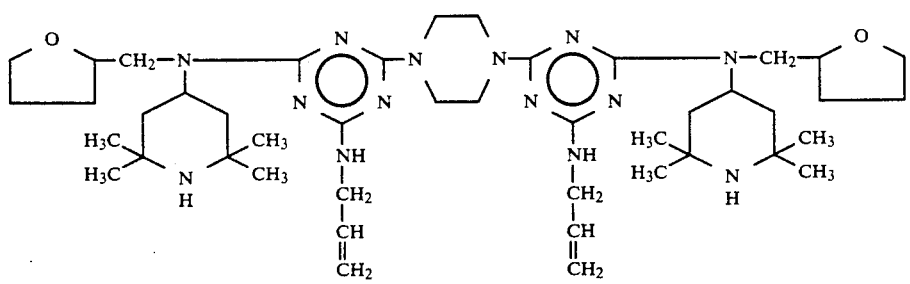

24.04 g (0.1 mol) of N-(2,2,6,6-tetramethyl-4-piperidyl)-tetrahydrofurfurylamine dissolved in 50 ml of xylene are added to a solution of 20.50 g (0.1 mol) of 2-allylamino-4,6-dichloro-1,3,5-triazine in 150 ml of xylene. The mixture is heated for 4 hours at 60° C. and cooled to ambient temperature, and a solution of 4.10 g (0.11 mol) of sodium hydroxide in 30 ml of water is added.

After 5 hours' heating at 60° C., the mixture is cooled, the aqueous phase is separated off and 4.31 g (0.05 mol) of piperazine are added. The mixture is heated under reflux for 4 hours and, after the addition of 8.80 9 (0.22 mol) of sodium hydroxide at ambient temperature, heating under reflux is continued for 20 hours, with azeotropic removal of the added water and of the water of reaction. p The mixture is then cooled to 60° C., filtered and concentrated.

On cooling, a product of melting point 210°–211° C. crystallizes.

Analysis for $C_{44}H_{74}N_{14}O_2$. Calculated: C=63.58%; H=8.97%; N=23.59%. Found: C=63.37%; H=8.85%; N=23.47%.

EXAMPLE 13

Preparation of the compound

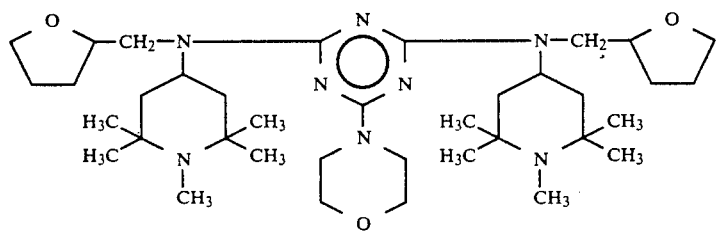

64.29 g (0.1 mol) of the compound from Example 4, 250 ml of xylene, 12.02 g (0.4 mol) of paraformaldehyde, 4 g of 5% palladium-on-carbon, containing 50% of water, and 80 ml of water are introduced into a 1 liter autoclave.

After flushing with nitrogen, hydrogenation is carried out at 130° C. under a pressure of 20 bar.

After the absorption of hydrogen has ceased, the reaction mixture is cooled to ambient temperature, the catalyst is filtered off, and the filtrate is evaporated in vacuo.

This gives a product of melting point 130°–132° C.

Analysis for $C_{37}H_{66}N_8O_3$. Calculated: C=66.22%; H 32 9.90%; N=16.71%. Found: C=66.29%; H=9.84%; N=16.64%.

Example 14

Preparation of the compound

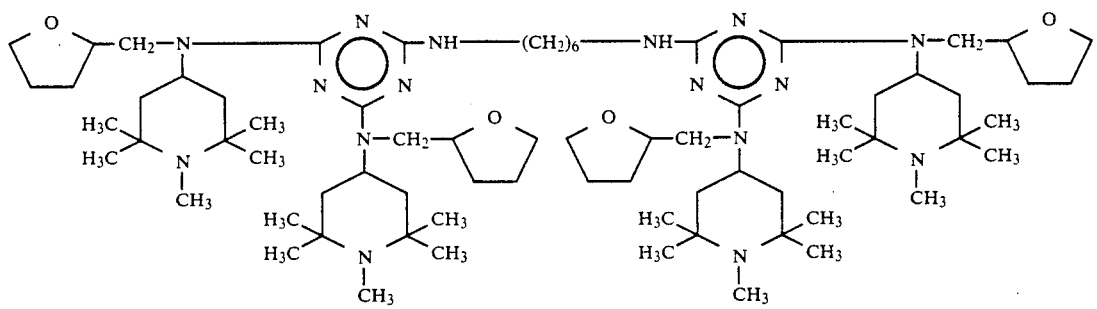

A mixture composed of 3.59 g (0.078 mol) of formic acid and a solution obtained by dissolving 2.43 9 (0.081 mol) of paraformaldehyde in 20 ml of a 2% aqueous sodium hydroxide solution are added slowly in 2 hours to a solution, heated to 115° C., of 20.86 g (0.017 mol) of the product from Example 8 in 55 ml of xylene; the water added and the water of reaction are azeotropically removed simultaneously during the addition.

The mixture is cooled to 60° C., a solution of 4.00 g (0.1 mol) of sodium hydroxide in 30 ml of water is added, and heating is carried out for 1 hour at 60° C.

After the aqueous phase has been separated off, the mixture is dried by separating the water off azeotropically and then evaporated, which gives a product of melting point 123°–125° C.

Analysis for $C_{72}H_{130}N_{16}O_4$. Calculated: C=67.36%; H=10.21%; N=17.45%. Found: C=66.69%; H=10.09%; N=16.82%.

EXAMPLES 15

Following the procedure describe using the appropriate reagents and molar ratios, the following compounds of the formula:

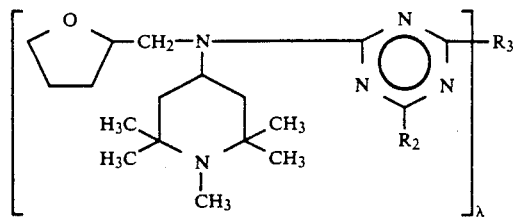

are prepared:

| Example | $R_2$ | $\lambda$ | $R_3$ | Melting point (°C.) |
|---|---|---|---|---|
| 15 | -O-(2,2,6,6-tetramethyl-1-methylpiperidin-4-yl) | 1 | -O-(2,2,6,6-tetramethyl-1-methylpiperidin-4-yl) | 78–80 |
| 16 | -N(C4H9)-(1,2,2,6,6-pentamethylpiperidin-4-yl) | 1 | -N(C4H9)-(1,2,2,6,6-pentamethylpiperidin-4-yl) | 91–93 |
| 17 | -N(CH2-tetrahydrofurfuryl)-(1,2,2,6,6-pentamethylpiperidin-4-yl) | 1 | -NH-C(CH3)2-CH2-C(CH3)3 | 75–77 |
| 18 | -N(CH2-tetrahydrofurfuryl)-(1,2,2,6,6-pentamethylpiperidin-4-yl) | 1 | -O-(2,2,6,6-tetramethyl-1-methylpiperidin-4-yl) | 83–85 |
| 19 | -N(CH2-tetrahydrofurfuryl)-(1,2,2,6,6-pentamethylpiperidin-4-yl) | 2 | -N-(CH2)6-N- bis(1,2,2,6,6-pentamethylpiperidin-4-yl) | 168–170 |
| 20 | -N(CH2-tetrahydrofurfuryl)-(1,2,2,6,6-pentamethylpiperidin-4-yl) | 3 | -NH-(CH2)2-N-(CH2)2-NH- | 155–157 |

-continued

| Example | R₂ | λ | R₃ | Melting point (°C.) |
|---|---|---|---|---|
| 21 | 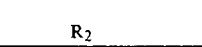 | 4 |  | 165-167 |

EXAMPLE 22

Preparation of the compound

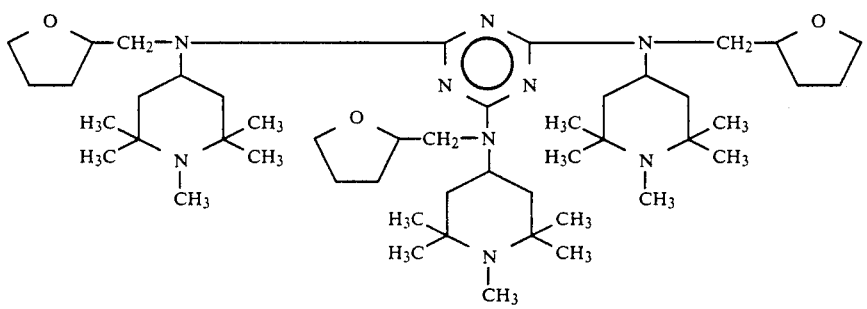

39.81 g (0.05 mol) of the product from Example 7 are dissolved in a solution of 23.01 g (0.05 mol) of formic acid in 250 ml of water.

13.51 g (0.45 mol) of paraformaldehyde are added, and the mixture is heated under reflux for 10 hours. After cooling to ambient temperature, a solution of 21.38 g (0.53 mol) of sodium hydroxide in 60 ml of water is added. A precipitate forms, which is extracted with 200 ml of dichloromethane. The organic solution is washed repeatedly with water, dried over sodium sulfate and evaporated.

The product has a melting point of 119°-121° C.

Analysis for $C_{48}H_{87}N_9O_3$. Calculated: C=68.78%; H=10.46%; N=15.04%. Found: C=68.19%; H=10.36%; N=15.17%.

EXAMPLE 23

Antioxidant action in polypropylene plaques: 1 g of each of the compounds indicated in Table 1 and 1 g of calcium stearate are mixed in a slow mixer with 1,000 g of polypropylene powder of melt index =2 g/10 minutes (measured at 230° C. and 2.16 kg).

The mixtures are extruded twice at 200°-220° C. to give polymer granules which are then converted into plaques of 1 mm thickness by compression-molding at 230° C for 6 minutes.

The plaques are then punched using a DIN 53451 mold, and the specimens obtained are exposed in a forced-circulation air oven maintained at a temperature of 135° C.

The specimens are checked at regular intervals by folding them by 180o in order to determine the time (in hours) required for fracturing them. The results obtained are given in Table 1.

TABLE 1

| Stabilizer | Time to fracture (hours) |
|---|---|
| Without stabilizer | 250 |
| Compound from Example 2 | 1,960 |
| Compound from Example 4 | 1,240 |
| Compound from Example 5 | 1,740 |
| Compound from Example 7 | 1,630 |
| Compound from Example 13 | 1,610 |
| Compound from Example 14 | 1,220 |
| Compound from Example 22 | 1,690 |

EXAMPLE 24

Light-stabilizing action in polypropylene tapes: 1 g of each of the compounds indicated in Table 2, 0.5 g of tris-(2,4-di-t-butylphenyl) phosphite, 0.5 g of pentaerythritol tetrakis-]3-(3,5-di-t-butyl-4-hydroxyphenyl)-propionate and 1 g of calcium stearate are mixed in a slow mixer with 1,000 g of polypropylene powder of melt index=2 g /10 minutes (measured at 230° C. and 2.16 kg).

The mixtures are extruded at 200°-220° C. to give polymer granules which are then converted into stretched tapes of 50 μm thickness and 2.5 mm width, using a pilot-type apparatus (Leonard-Sumirago (VA) Italy) and operating under the following conditions:

Extruder temperature: 210°-230° C.

Head temperature: 240°-260° C.

Stretch ratio: 1:6.

The tapes thus prepared are exposed, mounted on a white card, in a Weather-0-Meter 65 WR (ASTM G26-77) at a black panel temperature of 63° C.

The residual tenacity is measured on samples, taken after various times of exposure to light, by means of a constant-speed tensometer; the exposure time (in hours) needed to halve the initial tenacity ($T_{50}$) is then calculated.

Tapes prepared under the same conditions as indicated above, but without the addition of stabilizer, are exposed for comparison.

The results obtained are shown in Table 2:

TABLE 2

| Stabilizer | $T_{50}$ (hours) |
|---|---|
| Without stabilizer | 500 |
| Compound from Example 1 | 2,690 |
| Compound from Example 2 | 2,440 |
| Compound from Example 7 | 2,030 |
| Compound from Example 13 | 2,000 |
| Compound from Example 14 | 2,050 |
| Compound from Example 15 | 2,420 |
| Compound from Example 22 | 2,130 |

What is claimed is:
1. A compound of formula I

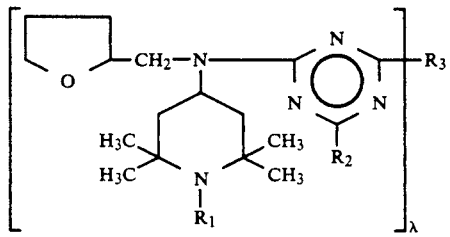

in which $R_1$ is hydrogen, $C_1-C_8$alkyl, $O_1$, OH, NO, $CH_2CN$, $C_1-C_{18}$alkoxy, $C_5-C_{12}$cycloalkoxy, $C_3-C_6$alkenyl, $C_7-C_9$phenylalkyl which is unsubstituted or mono-, di- or tri-substituted on the phenyl by $C_1-C_4$alkyl, $C_1-C_8$acyl or $C_2-C_4$alkyl substituted by OH in the 2-, 3- or 4 -position, $R_2$ is a group —$OR_4$, —$SR_4$ or

in which $R_4$ is $C_1-C_{18}$alkyl, $C_5-C_{12}$cycloalkyl which is unsubstituted or mono-, di- or tri-substituted by $C_1-C_4$alkyl, $C_3-C_{18}$alkenyl, phenyl which is unsubstituted or mono-, di- or tri-substituted by $C_1-C_4$alkyl, $C_7-C_9$phenylalkyl which is unsubstituted or mono-, di- or tri-substituted on the phenyl by $C_1-C_4$alkyl, or a group of the formula (II)

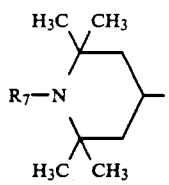

where $R_7$ has any of the definitions of $R_1$, $R_5$ and $R_6$ which can be identical or different are hydrogen, $C_1-C_{18}$alkyl, $C_5-C_{12}$cycloalkyl which is unsubstituted or mono-, di- or tri-substituted by $C_1-C_4$alkyl, $C_7-C_9$phenylalkyl which is unsubstituted or mono-, di- or tri-substituted on the phenyl by $C_1-C_4$alkyl, $C_2-C_4$alkyl which is substituted in the 2-, 3- or 4- position by OH, by $C_1-C_8$alkoxy or by di-($C_1-C_4$alkyl)-amino, $C_3-C_{18}$alkenyl, tetrahydrofurfuryl or a group of the formula (II), or $R_5$ and $R_6$, together with the nitrogen atom to which they are linked, form part of a 5-membered to 7-membered heterocyclic ring which is 1-pyrrolidyl, 1-piperidyl, 4-morpholinyl, 4-methyl-1-piperazinyl, 1-hexahydroazepinyl, 5,5,7-trimethyl-1-homopiperazinyl or 4,5,5,7-tetramethyl -1homopiperazinyl, λ is an integer from 1 to 6, and, if λ is 1, $R_3$ has any of the definitions of $R_2$, with the proviso that $R_2$ and $R_3$ are different from

if both $R_5$ and $R_6$ are a group of the formula (II), and; if λ is 2, $R_3$ is one of the groups of the formulae (IIIa)–(IIIc)

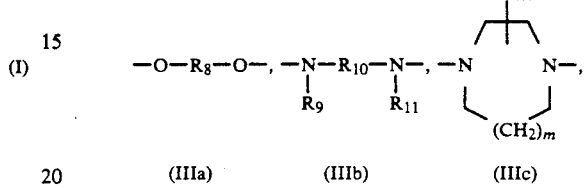

(IIIa)    (IIIb)    (IIIc)

in which $R_8$ is $C_2-C_{12}$alkylene, cyclohexylene, cyclohexylenedimethylene, methylenedicyclohexylene, ($C_2-C_6$alkylidene)-dicyclohexylene, phenylene, ($C_1-C_6$alkylidene)-diphenylene or xylylene, $R_9$ and $R_{11}$ which can be identical or different are hydrogen, $C_1-C_{18}$alkyl, $C_5-C_{12}$cycloalkyl which is unsubstituted or mono-, di- or tri-substituted by $C_1-C_4$alkyl, $C_7-C_9$phenylalkyl which is unsubstituted or mono-, di- or tri-substituted on the phenyl by $C_1-C_4$alkyl, or a group of the formula (II), $R_{10}$ is as defined above for $R_8$ or is $C_4-C_{12}$alkylene interrupted by 1, 2 or 3 oxygen atoms or by 1 or 2 groups >N—$R_{13}$, where $R_{13}$ has any of the definitions of $R_9$ and $R_{11}$, or is one of the groups of the formulae (IVa)–(IVd)

—$COR_{14}$,  —$COOR_{15}$,  —$COCOOR_{15}$,  —$SO_2R_{16}$ (IVa)    (IVb)    (IVc)    (IVd)

where $R_{14}$ is hydrogen, $C_1-C_{18}$alkyl, $C_5-C_{12}$cycloalkyl which is unsubstituted or mono-, di- or tri-substituted by $C_1-C_4$alkyl, $C_2-C_{18}$alkenyl, phenyl which is unsubstituted or mono-, di- or tri-substituted by $C_1-C_4$alkyl and/or an OH group, $C_7-C_9$phenylalkyl which is unsubstituted or mono-, di- or tri-substituted on the phenyl by $C_1-C_4$alkyl and/or an OH group, $R_{15}$ is $C_1-C_{18}$alkyl, $C_5-C_{12}$cycloalkyl which is unsubstituted or mono-, di- or tri-substituted by $C_1-C_4$alkyl, $C_3-C_{18}$alkenyl or a group of the formula (II) and $R_{16}$ is $C_1-C_{18}$alkyl or phenyl which is unsubstituted or mono-, di- or tri-substituted by $C_1-C_4$alkyl, m is zero or 1, $R_{12}$ is hydrogen or methyl and n is zero, 1, 2, 3 or 4, and, if λ is 3, $R_3$ is one of the groups of the formulae (VA)–(VC)

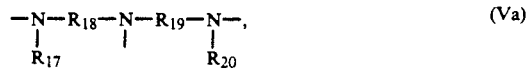 (Va)

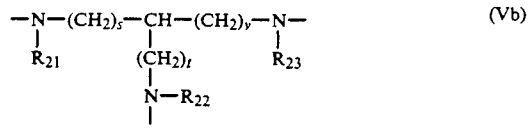 (Vb)

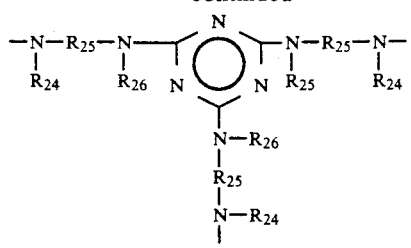
(IVc)

in which $R_{17}$, $R_{20}$, $R_{21}$, $R_{22}$, $R_{23}$, $R_{24}$ and $R_{26}$ which can be identical or different are as defined above for $R_9$ and $R_{11}$; $R_{18}$ and $R_{19}$ which can be identical or different are $C_2$–$C_{12}$alkylene or $C_4$–$C_{12}$alkylene interrupted by a group >N—$R_{27}$ with $R_{27}$ being as defined above for $R_{13}$, s and v which can be identical or different are integers from 2 to 6, t is zero of 1 and $R_{25}$ is $C_2$–$C_{12}$alkylene, and, if λ is 4, 5 or 6, $R_3$ is a group of the formula

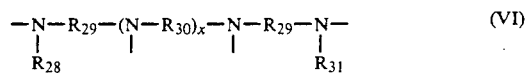
(VI)

in which $R_{28}$ and $R_{31}$ which can be identical or different are as defined above for $R_9$ and $R_{11}$; $R_{29}$ and $R_{30}$ which can be identical or different are $C_2$–$C_{12}$alkylene and x is 1, 2 or 3, and, if λ is 4, $R_3$ is also one of the groups of the formulae (VIIa)–(VIIc)

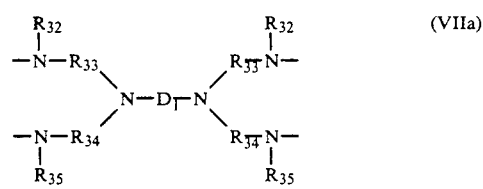
(VIIa)

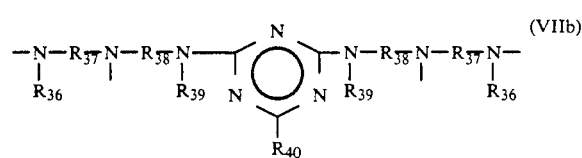
(VIIb)

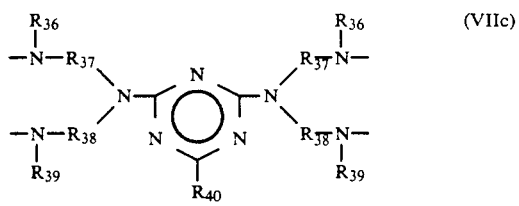
(VIIc)

in which $R_{32}$, $R_{35}$, $R_{36}$ and $R_{39}$ which can be identical or different are as defined above for $R_9$ and $R_{11}$; $R_{33}$, $R_{34}$, $R_{37}$ and $R_{38}$ which can be identical or different are $C_2$–$C_{12}$alkylene, $D_1$ is $C_2$–$C_{12}$alkylene, 2-hydroxytrimethylene, —CH$_2$CO—, xylylene or one of the groups of the formulae (VIIIa) and (VIIIb)

—COR$_{41}$CO—, —COOR$_{42}$OOC—

(VIIIa)        (VIIIb)

in which $R_{41}$ is a direct bond, $C_1$–$C_{12}$alkylene, cyclohexylene or phenylene and $R_{42}$ is as defined above for $R_8$, and $R_{40}$ is as defined above for $R_2$, and, if λ is 6, $R_3$ is also one of the groups of the formulae (IXa)–(IXc)

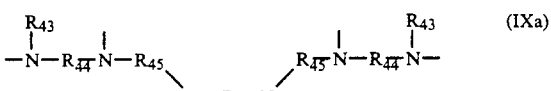
(IXa)

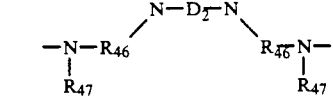

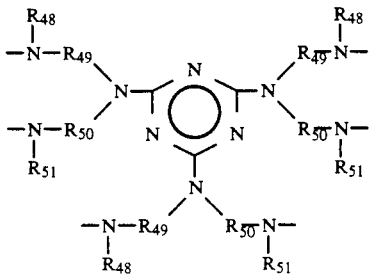
(IXb)

(IXc)

in which $R_{43}$, $R_{47}$, $R_{48}$ and $R_{51}$ which can be identical or different are as defined above for $R_9$ and $R_{11}$; $R_{44}$, $R_{45}$, $R_{46}$, $R_{49}$ and $R_{50}$ which can be identical or different are $C_2$–$C_{12}$alkylene and $D_2$ is as defined above for $D_1$.

2. A compound of the formula (I) according to claim 1, wherein $R_1$ is hydrogen, $C_1$–$C_4$alkyl, OH, $C_6$–$C_{12}$alkoxy, $C_5$–$C_8$cycloalkoxy, allyl, benzyl, acetyl or 2-hydroxyethyl.

3. A compound of the formula (I) according to claim 1, wherein $R_2$ is a group —OR$_4$, —SR$_4$ or

in which $R_4$ is $C_1$–$C_{18}$alkyl, $C_5$–$C_8$cycloalkyl which is unsubstituted or mono-, di- or tri-substituted by $C_1$–$C_4$alkyl, $C_3$–$C_{12}$alkenyl, phenyl, benzyl or a group of the formula (II), $R_5$ and $R_6$ which can be identical or different are hydrogen, $C_1$–$C_{18}$alkyl, $C_5$–$C_8$cycloalkyl which is unsubstituted or mono-, di- or tri-substituted by $C_1$—$C_4$alkyl, benzyl, $C_2$–$C_3$alkyl substituted in the 2- or 3-position by OH, by $C_1$–$C_4$alkoxy or by di-($C_1$–$C_4$alkyl)-amino, allyl, oleyl, tetrahydrofurfuryl or a group of the formula (II), or the group

is 1-pyrrolidyl, 1-piperidyl, 4-morpholinyl or 1-hexahydroazepinyl, and λ is an integer from 1 to 6, and, if λ is 1, $R_3$ has any of the definitions of $R_2$ with the proviso that $R_2$ and $R_3$ are different from

if both $R_5$ and $R_6$ are a group of the formula (II), and, if $\lambda$ is 2, $R_3$ is one of the groups of the formula (IIa)–(IIIc) in which $R_8$ is $C_2$–$C_{10}$alkylene, cyclohexylene, cyclohexylenedimethylene, methylenedicyclohexylene, isopropylidenedicyclohexylene, phenylene or isopropylidenediphenylene, $R_9$ and $R_{11}$ which can be identical or different are hydrogen, $C_1$–$C_{12}$alkyl, $c_5$–$C_8$cycloalkyl which is unsubstituted or mono-, di- or tri-substituted by $C_1$–$C_4$alkyl, benzyl or a group of the formula (II), $R_{10}$ is as defined above for $R_8$ or is $C_4$–$C_{12}$alkylene interrupted by 1, 2 or 3 oxygen atoms or by 1 or 2 groups $>N-R_{13}$ where $R_{13}$ has any of the definitions given for $R_9$ and $R_{11}$, or is one of the groups of the formulae (IVa)–(IVd) in which $R_{14}$ is hydrogen, $C_1$–$C_{17}$alkyl, $C_5$–$C_8$cycloalkyl which is unsubstituted or mono-, di- or tri-substituted by $C_1$–$C_4$alkyl, $C_2$–$C_{17}$alkenyl, phenyl which is unsubstituted or mono-, di- or tri-substituted by $C_1$–$C_4$alkyl and/or an OH group, $C_7$–$C_8$phenylalkyl which is unsubstituted or mono-, di- or tri-substituted on the phenyl by $C_1$–$C_4$alkyl and/or an OH group, $R_{15}$ is $C_1$–$C_{18}$alkyl, $C_5$–$C_8$cycloalkyl which is unsubstituted or mono-, di- or tri-substituted by $C_1$–$C_4$alkyl, $C_3$–$C_{18}$alkenyl or a group of the formula (II) and $R_{16}$ is $C_1$–$C_{12}$alkyl, phenyl or tolyl, m is zero or 1, $R_{12}$ is hydrogen or methyl and n is zero, 1, 2, 3 or 4, and, if $\lambda$ is 3, $R_3$ is one of the groups of the formulae (Va)–(Vc) in which $R_{17}$, $R_{20}$, $R_{21}$, $R_{22}$, $R_{23}$, $R_{24}$ and $R_{26}$ which can be identical or different are as defined above for $R_9$ and $R_{11}$; $R_{18}$ and $R_{19}$ which can be identical or different are $C_2$–$C_{10}$alkylene or $C_4$–$C_{12}$alkylene interrupted by a group $>N-R_{27}$ with $R_{27}$ being as defined above for $R_{13}$, s and v which can be identical or different are integers from 2 to 6, t is zero or 1 and $R_{25}$ is $C_2$–$C_{10}$alkylene, and, if $\lambda$ is 4, 5 or 6, $R_3$ is a group of the formula (VI) in which $R_{28}$ and $R_{31}$ which can be identical or different are as defined above for $R_9$ and $R_{11}$; $R_{29}$ and $R_{30}$ which can be identical or different are $C_2$–$C_{10}$alkylene and x is 1, 2 or 3, and, if $\lambda$ is 4, $R_3$ is also one of the groups of the formulae (VIIa)–(VIIc) in which $R_{32}$, $R_{35}$, $R_{36}$ and $R_{39}$ which can be identical or different are as defined above for $R_9$ and $R_{11}$; $R_{33}$, $R_{34}$, $R_{37}$ and $R_{38}$ which can be identical or different are $C_2$–$C_{10}$alkylene, $D_1$ is $C_2$–$C_{10}$alkylene, 2-hydroxytrimethylene, —CH$_2$CO—, xylylene or one of the groups of the formulae (VIIIa) or (VIIIb) in which $R_{41}$ is a direct bond or $C_1$–$C_{10}$alkylene, $R_{42}$ is as defined above for $R_8$, and $R_{40}$ is as defined above for $R_2$, and, if $\lambda$ is 6, $R_3$ is also one of the groups of the formulae (IXa)–(IXc) in which $R_{43}$, $R_{47}$, $R_{48}$ and $R_{51}$ which can be identical or different are as defined above for $R_9$ and $R_{11}$; $R_{44}$, $R_{45}$, $R_{46}$, $R_{49}$ and $R_{50}$ which can be identical or different are $C_2$–$C_{10}$alkylene and $D_2$ is as defined above for $D_1$.

4. A compound of the formula (I) according to claim 1, wherein $R_2$ is a group —$OR_4$ or

in which $R_4$ is $C_1$–$C_{12}$alkyl, cyclohexyl which is unsubstituted or mono-, di- or tri-substituted by $C_1$–$C_4$alkyl, allyl, undecenyl, phenyl, benzyl or a group of the formula (II), $R_5$ and $R_6$ which can be identical or different are hydrogen, $C_1$–$C_{12}$alkyl, cyclohexyl which is unsubstituted or mono-, di- or tri-substituted by $C_1$–$C_4$alkyl, benzyl, $C_2$–$C_3$alkyl which is substituted in the 2- or 3-position by OH, by methoxy, by ethoxy, by dimethylamino or by diethylamino, allyl, tetrahydrofurfuryl or a group of the formula (II), or the group

is 4-morpholinyl, and l is an integer from 1 to 6, and, if $\lambda$ is 1, $R_3$ has any of the definitions given for $R_2$, with the proviso that $R_2$ and $R_3$ are different from

if both $R_5$ and $R_6$ are a group of the formula (II), and if $\lambda$ is 2, $R_3$ is one of the groups of the formulae (IIIb)–(IIIc) in which $R_9$ and $R_{11}$ which can be identical or different are hydrogen, $C_1$–$C_8$alkyl, cyclohexyl which is unsubstituted or mono-, di- or tri-substituted by $C_1$–$C_4$alkyl, benzyl or a group of the formula (II), $R_{10}$ is $C_2$–$C_8$alkylene, cyclohexylenedimethylene, methylenedicyclohexylene, $C_4$–$C_{10}$alkylene interrupted by 1 or 2 oxygen atoms or $C_4$–$C_{12}$alkylene interrupted by 1 or 2 groups $>N-R_{13}$ where $R_{13}$ has any of the definitions given for $R_9$ and $R_{11}$, or is one of the groups of the formulae (IVa)–(IVc) in which $R_{14}$ is $C_1$–$C_{12}$alkyl, cyclohexyl which is unsubstituted or mono-, di- or tri-substituted by $C_1$–$C_4$alkyl, $C_2$–$C_{10}$alkenyl, phenyl, 3,5-di-t-butyl-4-hydroxyphenyl, benzyl or 2-(3,5-di-t-butyl-4-hydroxyphenyl)-ethyl, $R_{15}$ is $C_1$–$C_{12}$alkyl, cyclohexyl which is unsubstituted or mono-, di- or tri-substituted by $C_1$–$C_4$alkyl, allyl, undecenyl, oleyl or a group of the formula (II), m is zero or 1, $R_{12}$ is hydrogen or methyl and n is zero, 1, 2 or 3, and, if $\lambda$ is 3, $R_3$ is a group of the formula (Va) in which $R_{17}$ and $R_{20}$ which can be identical or different are as defined above for $R_9$ and $R_{11}$; $R_{18}$ and $R_{19}$ which can be identical or different are $C_2$–$C_8$alkylene and $R_{18}$ is also $C_4$–$C_{12}$alkylene interrupted by a group $>N-R_{27}$ with $R_{27}$ being as defined above for $R_{13}$, and, if $\lambda$ is 4, 5 or 6, $R_3$ is a group of the formula (VI) in which $R_{28}$ and $R_{31}$ which can be identical or different are as defined above for $R_9$ and $R_{11}$; $R_{29}$ and $R_{30}$ which can be identical or different are $C_2$–$C_8$alkylene and x is 1, 2 or 3, and, if $\lambda$ is 4, $R_3$ is also a group of the formula (VIIa) in which $R_{32}$ and $R_{35}$ which can be identical or different are as defined above for $R_9$ and $R_{11}$; $R_{33}$ and $R_{34}$ which can be identical or different are $C_2$–$C_8$alkylene and $D_1$ is $C_2$–$C_8$alkylene, 2-hydroxytrimethylene, xylylene or a group of the formula (VIIIa) or (VIIIb) in which $R_{41}$ is a direct bond or $C_1$–$C_8$alkylene and $R_{42}$ is $C_4$–$C_8$alkylene, 3-oxapentane-1,5-diyl, cyclohexylenedimethylene or isopropylidenedicyclohexylene, and, if $\lambda$ is 6, $R_3$ is also a group of the formula (IXa) in which $R_{43}$ and $R_{47}$ which can be identical or different are as defined above for $R_9$ and $R_{11}$; $R_{44}$, $R_{45}$ and $R_{46}$ which can be identical of different are $C_2$–$C_8$alkylene and $D_2$ is as defined above for $D_1$.

5. A compound of the formula (I) according to claim 1, wherein $R_2$ is a group —$OR_4$ or

in which $R_4$ is $C_1-C_8$alkyl, cyclohexyl, allyl, phenyl, benzyl, 2,2,6,6-tetramethyl-4-piperidyl or 1,2,2,6,6-pentamethyl4-piperidyl, $R_5$ and $R_6$ which can be identical or different are $C_1-C_8$alkyl, cyclohexyl, benzyl, $C_2-C_3$alkyl substituted in the 2- or 3-position by methoxy, by ethoxy, by dimethylamino or by diethylamino, allyl, tetrahydrofurfuryl, 2,2,6,6-tetramethyl-4-piperidyl or 1,2,2,6,6-pentamethyl-4-piperidyl, or $R_5$ is also hydrogen, or the group

is 4-morpholinyl, and l is 1, 2, 3 or 4, and, if $\lambda$ is 1, $R_3$ has any of the definitions given for $R_2$, with the proviso that $R_2$ and $R_3$ are different from

if both $R_5$ and $R_6$ are a group of the formula (II), and, if l is 2, $R_3$ is one of the groups of the formulae (IIIb)-(IIIc) in which $R_9$ and $R_{11}$ which can be identical or different are hydrogen, $C_1-C_4$alkyl, cyclohexyl, 2,2,6,6-tetramethyl-4-piperidyl or 1,2,2,6,6-pentamethyl-4-piperidyl, $R_{10}$ is $C_2-C_6$alkylene, cyclohexylenedimethylene, methylenedicyclohexylene, $C_4-C_{10}$alkylene interrupted by 1 or 2 oxygen atoms or $C_4-C_{12}$alkylene interrupted by 1 or 2 groups $>N-R_{13}$ in which $R_{13}$ is hydrogen, methyl or a group of the formula (IVa) or (IVb) in which $R_{14}$ is $C_1-C_8$alkyl, cyclohexyl, phenyl or 2-(3,5-di-t-butyl-4-hydroxyphenyl)-ethyl and $R_{15}$ is $C_1-C_8$alkyl, cyclohexyl, t-butylcyclohexyl or 1,2,2,6,6-pentamethyl-4-piperidyl, and m and n are zero and, if $\lambda$ is 3, $R_3$ is a group of the formula (Va) in which $R_{17}$ and $R_{20}$ which can be identical or different are as defined above for $R_9$ and $R_{11}$; $R_{18}$ and $R_{19}$ which can be identical or different are $C_2-C_6$alkylene and $R_{18}$ is also $C_4-C_6$alkylene interrupted by a group $>N-R_{27}$ with $R_{27}$ being as defined above for $R_{13}$, and, if l is 4, $R_3$ is a group of the formula (VI) in which $R_{28}$ and $R_{31}$ which can be identical or different are as defined above for $R_9$ and $R_{11}$; $R_{29}$ and $R_{30}$ which can be identical or different are $C_2-C_6$alkylene and x is 1, or $R_3$ is a group of the formula (VIIa) in which $R_{32}$ and $R_{35}$ which can be identical or different are as defined above for $R_9$ and $R_{11}$; $R_{33}$ and $R_{34}$ which can be identical or different are $C_2-C_6$alkylene and $D_1$ is a group of the formula (VIIIa) or (VIIIb) in which $R_{41}$ is a direct bond or $C_1-C_4$alkylene and $R_{42}$ is $C_4-C_6$alkylene.

6. A compound of the formula (I) according to claim 1, wherein $R_1$ is hydrogen or methyl, $R_2$ is a group $-OR_4$ or

in which $R_4$ is $C_1\alpha C_4$alkyl, 2,2,6,6-tetramethyl-4-piperidyl or 1,2,2,6,6-pentamethyl-4-piperidyl, $R_5$ and $R_6$ which can be identical or different are $C_1-C_8$alkyl, allyl, tetrahydrofurfuryl, 2,2,6,6-tetramethyl-4-piperidyl or 1,2,2,6,6-pentamethyl-4-piperidyl, or $R_5$ is also hydrogen, or the group

is 4-morpholinyl, and $\lambda$ is 1, 2, 3 or 4, and, if $\lambda$ is 1, $R_3$ has any of the definitions given for $R_2$, with the proviso that $R_2$ and $R_3$ are different from bis-(2,2,6,6-tetramethyl-4-piperidyl)-amino and bis-(1,2,2,6,6-pentamethyl-4-piperidyl)-amino, and, if $\lambda$ is 2, $R_3$ is one of the groups of the formulae (IIIb)-(IIIc) in which $R_9$ and $R_{11}$ which can be identical or different are hydrogen, methyl, 2,6,6-tetramethyl-4-piperidyl or 1,2,2,6,6-pentamethyl-4-piperidyl, $R_{10}$ is $C_2-C_6$alkylene or $C_4-C_6$alkylene interrupted by a group $>N-R_{13}$ where $R_{13}$ is hydrogen, methyl or a group of the formula (IVa) or (IVb) in which $R_{14}$ and $R_{15}$ are $C_1-C_4$alkyl, and m and n are zero, and, if $\lambda$ is 3, $R_3$ is a group of the formula (Va) in which $R_{17}$ and $R_{20}$ which can be identical or different are as defined above for $R_9$ and $R_{11}$; $R_{18}$ and $R_{19}$ which can be identical or different are $C_2-C_6$alkylene, and $R_{18}$ is also $C_4-C_6$alkylene interrupted by a group $>N-R_{27}$ with $R_{27}$ being as defined above for $R_{13}$, and if l is 4, $R_3$ is a group of the formula (VI) in which $R_{28}$ and $R_{31}$ which can be identical or different are hydrogen or methyl, $R_{29}$ and $R_{30}$ which can be identical or different are $C_2-C_3$alkylene and x is 1, or $R_3$ is a group of the formula (VIIa) in which $R_{32}$ and $R_{35}$ which can be identical or different are hydrogen, methyl, 2,2,6,6-tetramethyl-4-piperidyl or 1,2,2,6,6-pentamethyl-4-piperidyl, $R_{33}$ and $R_{34}$ which can be identical or different are $C_2-C_6$alkylene and $D_1$ is a group of the formula (VIIIa) or (VIIIb) in which $R_{41}$ is a direct bond or $C_1-C_4$alkylene and $R_{42}$ is tetramethylene or hexamethylene.

7. The compound

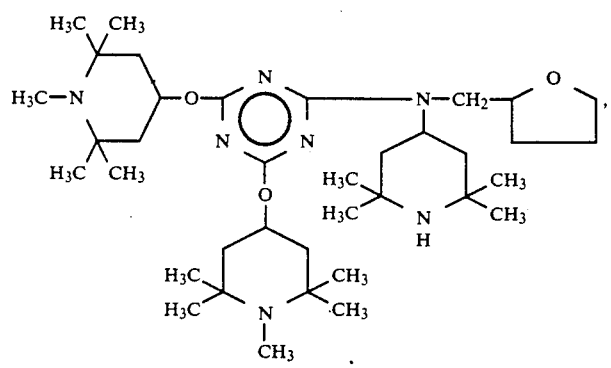

-continued
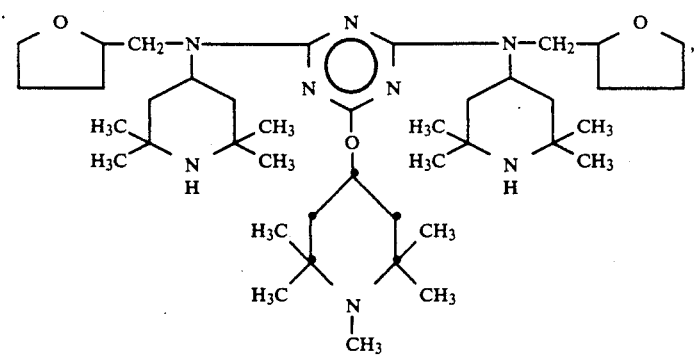
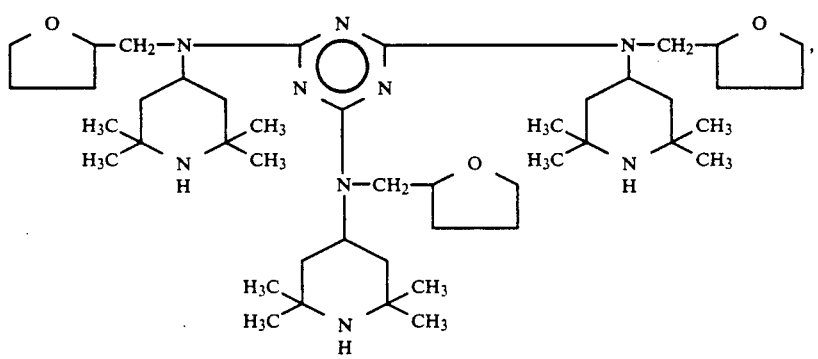
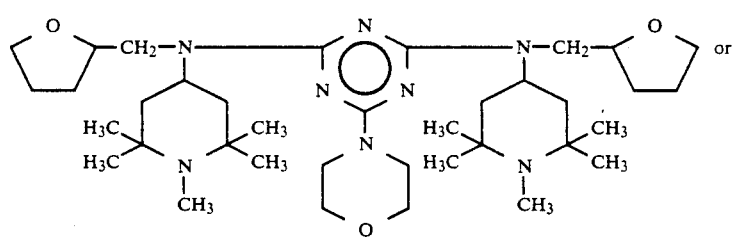
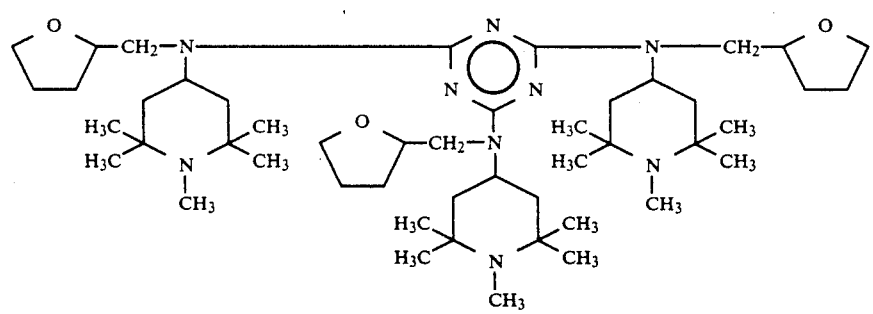
according to claim 1.